(12) United States Patent
Golz-Berner et al.

(10) Patent No.: US 6,403,062 B1
(45) Date of Patent: Jun. 11, 2002

(54) PERFUME COMPOSITION HAVING A SUN-BLOCK AND TANNING EFFECT

(75) Inventors: Karin Golz-Berner; Leonhard Zastrow, both of quai Jean-Charles Ray (MC)

(73) Assignee: Coty B.V. (NL)

( * ) Notice: Subject to any disclaimer, the term of this patent is extended or adjusted under 35 U.S.C. 154(b) by 0 days.

(21) Appl. No.: 09/763,594

(22) PCT Filed: Oct. 8, 1999

(86) PCT No.: PCT/DE99/03298

§ 371 (c)(1),
(2), (4) Date: Feb. 22, 2001

(87) PCT Pub. No.: WO00/21500

PCT Pub. Date: Apr. 20, 2000

(30) Foreign Application Priority Data

Oct. 9, 1998 (DE) .......................... 198 47 936

(51) Int. Cl.$^7$ ............................. A61K 7/42; A61K 7/44; A61K 7/00; A61K 7/46
(52) U.S. Cl. ............................. 424/59; 424/47; 424/60; 424/400; 424/401; 512/1; 514/844
(58) Field of Search ................................ 424/400, 401, 424/59, 60, 47; 512/1; 514/844

(56) References Cited

U.S. PATENT DOCUMENTS

| 4,968,497 | A | * | 11/1990 | Wolfram et al. ............... 424/59 |
| 5,540,853 | A | * | 7/1996 | Trinh et al. .................. 510/101 |
| 6,171,605 | B1 | * | 1/2001 | Bevacqua et al. .......... 424/401 |
| 6,231,837 | B1 | * | 5/2001 | Stroud et al. ................. 424/59 |

* cited by examiner

*Primary Examiner*—Jose G. Dees
*Assistant Examiner*—Marine Lamm
(74) *Attorney, Agent, or Firm*—Pendorf & Cutliff

(57) ABSTRACT

The invention relates to a perfume composition which, at the same time, has a tanning effect or both a sun-block and tanning effect. According to the invention, the perfume composition having a tanning effect or both a sun-block and tanning effect is comprised of a clear hydroalcoholic solution. Said solution contains an alcohol-soluble, organic sunscreen filter in a proportion of 0.05 to 12 wt. %; dihydroxyacetone in a proportion of 0.5 to 10 wt. %; one or more monovalent alcohols with 3 to 5 carbon atoms in a proportion of 30 to 85 wt. %; one or more polyvalent alcohols with 3 to 5 carbon atoms in a proportion of 0.5 to 15 wt %; perfume oil in a proportion of 1 to 20 wt. %; and water in a proportion of 3 to 67.95 wt. %, hereby the proportions refer each time to the total composition.

13 Claims, No Drawings

PERFUME COMPOSITION HAVING A SUN-BLOCK AND TANNING EFFECT

BACKGROUND OF THE INVENTION

1. Field of the Invention

The invention relates to a perfume composition which, at the same time, has a self-tanning effect or both a sun-block and self-tanning effect.

2. Description of the Related Art

Up to now, a multiplicity of perfume compositions have been developed which concentrated in essence on different fragrance combinations or their encapsulation or binding to certain carrier substances such as perfume powder, perfume gels and perfume sprays. These products contain neither sun-blockers having specified sun protection factors nor self-tanning additives.

Dihydroxyacetone is a known self-tanning agent, which has the form of a white powder, but which tends to form more or less turbid dispersions when coming in contact with monovalent alcohols such as ethanol. This fact makes manufacturers generally describe its contact with ethanol as an incompatibility.

SUMMARY OF THE INVENTION

It is an object of the invention to provide a fragrance composition which, when brought onto the human skin, causes a tanning effect and, at the same time, may provide a sun-block effect on skin and hair.

DETAILED DESCRIPTION OF THE INVENTION

According to the invention, the perfume composition having a tanning effect or both a sun-block and tanning effect is comprised of a clear hydroalcoholic solution containing an alcohol-soluble, organic sunscreen filter in a proportion of 0.05 to 12 wt. %;

dihydroxyacetone in a proportion of 0.5 to 10 wt. %;

one or more monovalent alcohols with 3 to 5 carbon atoms in a proportion of 30 to 85 wt. %;

one or more polyvalent alcohols with 3 to 5 carbon atoms in a proportion of 0.5 to 15 wt. %;

perfume oil in a proportion of 1 to 20 wt. %; and water in a proportion of 3 to 67.95 wt. %; and wherein the proportions refer each time to the total composition.

Preferable dihydroxyacetone concentrations range between 3 and 8 wt. %, particularly between 4 and 7 wt. %.

The concentration of the alcohol-soluble organic sunscreen filter advantageously ranges between 1.5 and 10 wt. %.

The concentration of the perfume oil advantageously ranges between 1 and 15 wt. %.

Surprisingly, the disharmony usually occurring in contact with a monovalent alcohol such as ethanol, e.g. turbidity, does not occur in case of dihydroxyacetone, which may be due to the presence of the alcohol-soluble organic sunscreen filter, but this point has not yet become fully clear.

Preferably, octyl methoxycinnamate is used as organic sunscreen filter. Other suitable filters are benzophenone-3, butyl metoxybenzoylmethane or 4-methylbenzylidene camphor.

The proportion of monovalent alcohols preferably ranges between 40 and 80 wt. %. One particularly suitable alcohol is ethanol. Other possible alcohols are isopropanol and n-propanol.

The polyvalent alcohol used may for example be glycerine, a propane diol or a butane diol, advantageously also a mixture of two or more thereof. A preferred mixture comprises for example glycerine and 1.3-butane diol, particularly in proportions of 1:0.5 to 1:3.

In addition to the alcohol-soluble organic sunscreen filter, a water-soluble organic sunscreen filter may be contained, such as benzophenone-3 and phenyl benzimidazole sulfonic acid.

The concentration of these water-soluble filters may be in the range between 2 and 15 wt. %.

The perfume composition according to the invention may, if provided with the appropriate sunscreen filters, have a sun protection factor of 5 to 10.

Advantageously, the perfume composition according to the invention is provided as a spray, which may be either a pumping spray or a spray using a propellant.

Further, the invention relates to a method for the production of a perfume composition having a tanning effect or both a sun-block and tanning effect, wherein said method is characterised in that a mixture of 0.5 to 15 wt. % of one or more polyvalent alcohols with 3 to 5 carbon atoms, 0.5 to 10 wt. % of dihydroxyacetone, 0.05 to 12 wt. % of an organic alcohol-soluble sunscreen filter and water is produced by stirring said mixture for a period of 0.5 to 1.5 hours at 300 to 600 rpm and by adding to the solution obtained 30 to 85 wt. % of one or more monovalent alcohols with 3 to 5 carbon atoms and 3 to 13 wt. % of perfume oil under continuous stirring.

The clear solution obtained is of excellent stability and can be stored for several months.

Now the invention is explained in more detail using examples. All numerical values refer to weight percent unless specified otherwise.

EXAMPLE 1

Perfume Spray For Body and Face

| | |
|---|---|
| Distilled water | 8.0 |
| Glycerine | 4.0 |
| 1.3 butylene glycol | 4.0 |
| Dihydroxyacetone | 8.0 |
| Octyl methoxycinnamate | 2.0 |
| Perfume oil | 5.0 |
| Ethanol | ad 100 |

A mixture comprising the polyvalent alcohols, dihydroxyacetone, octyl methoxycinnamate and water was produced by stirring at room temperature for a period of 70 minutes at approximately 500 rpm. Ethanol and the perfume oil were added under stirring to the solution obtained.

EXAMPLE 2

Perfume Spray For Body and Face Having a Sun Protection Factor

| | |
|---|---|
| Distilled water | 10.0 |
| Glycerine | 2.5 |
| 1.3 butylene glycol | 3.5 |
| Dihydroxyacetone | 5.0 |
| Octyl methoxycinnamate | 7.5 |
| Benzophenone-4 | 5.0 |
| Perfume oil | 10.0 |

-continued

| | |
|---|---|
| Vitamin E | 1.0 |
| Ethanol | ad 100 |

The procedure was equal to that of example 1, wherein benzophenone-4 and vitamin E were added to the mixture produced before, and the entire resulting mixture was stirred for 75 minutes at 520 rpm. The solution obtained had a sun protection factor of SPF 10 and, at the same time, a self-tanning effect.

EXAMPLE 3
Perfume Spray For Hair Having a Sun Protection Factor

| | |
|---|---|
| Distilled water | 7.5 |
| Glycerine | 5.0 |
| Dihydroxyacetone | 3.0 |
| Octyl methoxycinnamate | 7.5 |
| Benzophenone-4 | 5.0 |
| Perfume oil | 13.0 |
| Vitamin E | 1.0 |
| Vitamin B | 1.0 |
| Ethanol | ad 100 |

The procedure was equal to that of example 2. The solution obtained had a slight self-tanning effect and a sun protection factor of SPF 10. The solution was filled into a spray can.

What is claimed is:

1. A perfume composition which has a tanning effect or both a sun-block and tanning effect comprising in a clear hydroalcoholic solution an alcohol-soluble, organic sunscreen filter in a proportion of 0.05 to 12 wt. %;

dihydroxyacetone in a proportion of 0.5 to 10 wt. %;

one or more monovalent alcohols with 2 to 5 carbon atoms in a proportion of 30 to 85 wt. %;

one or more polyvalent alcohols with 3 to 5 carbon atoms in a proportion of 0.5 to 15 wt. %;

perfume oil in a proportion of 1 to 20 wt. %; and water in a proportion of 3 to 67.95 wt. %; and wherein the proportions refer each time to the total composition.

2. A perfume composition according to claim 1, wherein the concentration of dihydroxyacetone ranges between 3 and 8 wt. %.

3. A perfume composition according to claim 2, wherein the concentration of dihydroxyacetone ranges between 4 and 7 wt. %.

4. A perfume composition according to claim 1, wherein the concentration of the alcohol-soluble organic sunscreen filter ranges between 1.5 and 10 wt. %.

5. A perfume composition according to claim 1, wherein the organic sunscreen filter is octyl methoxycinnamate.

6. A perfume composition according to claim 1, wherein the proportion of monovalent alcohols ranges between 40 and 80 wt. %.

7. A perfume composition according to claim 1, wherein the monovalent alcohol is ethanol.

8. A perfume composition according to claim 1, wherein the polyvalent alcohol is a mixture of glycerine and 1.3-butane diol.

9. A perfume composition according to claim 1, wherein additionally a water-soluble organic sunscreen filter is contained.

10. A perfume composition according to claim, wherein said composition has a sun protection factor between 5 and 10.

11. A perfume composition according to claim 1, wherein said composition is provided as a spray.

12. A method for the production of a perfume composition having a tanning effect or both a sun-block and tanning effect comprising the production of a mixture of 0.5 to 15 wt. % of one or more polyvalent alcohols with 3 to 5 carbon atoms, 0.5 to 10 wt. % of dihydroxyacetone, 0.05 to 12 wt. % of an organic alcohol-soluble sunscreen filter and water by stirring said mixture for a period of 0.5 to 1.5 hours at 300 to 600 rpm and the addition, under stirring, of 30 to 85 wt. % of one or more monovalent alcohols with 2 to 5 carbon atoms and 1 to 20 wt. % of perfume oil until a clear solution is obtained.

13. A perfume composition which has a tanning effect or both a sun-block and tanning effect comprising in a clear hydroalcoholic solution:

an alcohol-soluble, organic sunscreen filter in a proportion of 0.05% to 12 wt. %;

dihydroxyacetone in a proportion of 0.5 to 10 wt. %;

one or more monovalent alcohols with 2 to 5 carbon atoms in a proportion of 30 to 85 wt. %;

one or more polyvalent alcohols with 3 to 5 carbon atoms in a proportion of 0.5 to 15 wt %;

perfume oil in a proportion of 1 to 20 wt. %; and water in a proportion of 3 to 67.95 wt. %, wherein the proportions refer each time to the total composition, and wherein said alcohol-soluble organic sunscreen filter is present in sufficient amount to render said composition clear.

* * * * *